US012569284B2

(12) United States Patent
Wieland

(10) Patent No.: US 12,569,284 B2
(45) Date of Patent: Mar. 10, 2026

(54) SCREW HOLE ADAPTED FOR DIFFERENT SCREWS

(71) Applicant: Stryker European Operations Limited, Carrigtwohill (IE)

(72) Inventor: Manfred Wieland, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 62 days.

(21) Appl. No.: 18/431,396

(22) Filed: Feb. 2, 2024

(65) Prior Publication Data

US 2024/0261002 A1      Aug. 8, 2024

Related U.S. Application Data

(60) Provisional application No. 63/482,928, filed on Feb. 2, 2023.

(51) Int. Cl.
*A61B 17/72* (2006.01)

(52) U.S. Cl.
CPC ................................. *A61B 17/7241* (2013.01)

(58) Field of Classification Search
CPC ........................ A61B 17/7233; A61B 17/7241
See application file for complete search history.

(56) References Cited

U.S. PATENT DOCUMENTS

| | | |
|---|---|---|
| 7,247,157 B2 | 7/2007 | Prager et al. |
| 11,116,557 B2 | 9/2021 | Zander et al. |
| 2006/0111717 A1 | 5/2006 | Saueressig et al. |
| 2021/0369308 A1* | 12/2021 | Zander ............... A61B 17/7208 |

* cited by examiner

*Primary Examiner* — Andrew Yang

(74) *Attorney, Agent, or Firm* — Lerner David LLP

(57) ABSTRACT

An intramedullary nail includes a body extending from a proximal end to a distal end, the body defining a transverse bore extending through the body along a transverse bore axis, the transverse bore having a threaded first segment with a negative thread defined by a first segment root diameter and a first segment outer thread diameter, the transverse bore having a threaded second segment with a negative thread defined by a second segment root diameter and a second segment outer thread diameter, wherein the second segment root diameter is larger than the first segment root diameter. A surgical assembly includes the intramedullary nail and a locking ring configured to be disposed within the annular recess.

19 Claims, 6 Drawing Sheets

200

202

300

302

SCREW HOLE ADAPTED FOR DIFFERENT SCREWS

CROSS-REFERENCE TO RELATED APPLICATIONS

The present application claims priority to U.S. application Ser. No. 63/482,928 filed Feb. 2, 2023, the disclosure of which is incorporated herein by reference.

BACKGROUND OF THE INVENTION

With intramedullary nails, it is common to enhance fixation in the bone by inserting a fastener transversely through a bore in the nail. The fastener art is becoming more sophisticated, such that many different types of fasteners are available to achieve locking within the bone and nail. However, bore holes in intramedullary nails are often threaded in a manner that is configured to accept solely one type and configuration of locking screw, which hinders the ability to improve fixation methods.

There is a need to provide a surgeon with the autonomy to utilize different types of locking screws for a particular procedure while not requiring different iterations of intramedullary nails for each type of locking screw, and to ensure proper securement and fixation of fasteners within the nail and bone.

BRIEF SUMMARY OF THE INVENTION

A first aspect of the present invention is an intramedullary nail including a body extending from a proximal end to a distal end, the body defining a transverse bore extending through the body along a transverse bore axis, the transverse bore having a threaded first segment with a negative thread defined by a first segment root diameter and a first segment outer thread diameter, the transverse bore having a threaded second segment with a negative thread defined by a second segment root diameter and a second segment outer thread diameter, wherein the second segment root diameter is larger than the first segment root diameter.

In accordance with other embodiments of the first aspect, the threaded first and second segments may be abutted such that the negative threads of the threaded first and second diameters form a continuous negative thread. The transverse bore may further include an annular recess having a recess diameter larger than the second segment root diameter. The recess diameter may be larger than the second segment outer thread diameter. The annular recess may be disposed between ends of the threaded second segment. The threaded first and second segments and the annular recess may make up an entirety of the transverse bore. The threaded first segment and the threaded second segment may have identical thread pitches. The first segment outer thread diameter may be equal to the second segment outer thread diameter.

A second aspect of the present invention is a surgical assembly including the aforementioned intramedullary nail and a locking ring configured to be disposed within the annular recess.

In accordance with other embodiments of the second aspect, the locking ring may be comprised of an elastic material. The elastic material may be a polymer. The locking ring may be slotted such that the locking ring forms an incomplete annulus. The locking ring may have an inner surface on which a thread is disposed.

A third aspect of the present invention is a surgical assembly including the aforementioned intramedullary nail or the aforementioned surgical assembly, and a first screw having a threaded portion defining a root diameter, an outer thread diameter, and a pitch, wherein the outer thread diameter of the threaded portion of the first screw is greater than the second segment root diameter, such that the threaded portion of the first screw is disposed within the negative threads of both the threaded first and second segments of the transverse bore when the first screw is disposed within the transverse bore.

In accordance with other embodiments of the third aspect, the surgical assembly may further include a second screw having a threaded portion defining a root diameter, an outer thread diameter, and a pitch, wherein the outer thread diameter of the threaded portion of the second screw is greater than the first segment root diameter and smaller than the second segment root diameter, such that the threaded portion of the second screw is disposed within the negative thread of the threaded first segment of the transverse bore and is not disposed within the negative thread of the threaded second segment of the transverse bore when the first screw is disposed within the transverse bore. The pitch of the second screw may be different than the pitch of the first screw, the outer thread diameter of the second screw may be different than the outer thread diameter of the first screw, and/or the root diameter of the second screw may be different than the root diameter of the first screw. The transverse bore may include first and second identically configured transverse bores. The first screw may be disposed within the transverse bore and the second screw may be disposed within the second transverse bore. Each transverse bore may further include an annular recess having a recess diameter larger than the second segment root diameter, and the surgical assembly may further include first and second locking rings disposed within the annular recesses of the first and second transverse bores, respectively. The pitch of the second screw may be different than the pitch of the first screw, the outer thread diameter of the second screw may be different than the outer thread diameter of the first screw, and the root diameter of the second screw may be different than the root diameter of the first screw.

The present application is directed to a nail with a specifically configured bore that can accommodate multiple different designs and configurations of screws or fasteners. The internal thread of the nail that interacts with the different screws is designed in a way to accommodate and fix various screws within the bore, despite differences among the screws in pitch, thread, diameter, etc. In one embodiment, a proximal portion of the bore is designed to accommodate and engage with threads of different types of screws regardless of these dimensional differences. In that embodiment, a distal portion of the bore is designed and configured differently than the proximal end to permit insertion and accommodation of the distal portion of the screw, where, in some cases the screw is configured to continue to engage threads of the distal part of the bore. The bore further includes a distal, annular recess which accommodates a locking ring. The locking ring is dimensioned so that it engages all screws configured to fit within the bore. In this way, despite the exact nature of the fixation and meeting of a particular screw with the bore, the locking ring provides a distal location within the bore at which the screw can mate with and secure its location within the bore through interaction with the locking ring as a bridge from the nail to the screw. The locking ring may be a split ring and may be elastic for flexing and accommodating the screw, and may also be of a material that yields to the threads of the screw to permit stronger fixation between the nail and the screw.

BRIEF DESCRIPTION OF THE DRAWINGS

The drawings described herein are for illustrative purposes only of the selected embodiments and are not all possible implementations and thus are not intended to limit the scope of the present disclosure.

DETAILED DESCRIPTION

Figure 1:
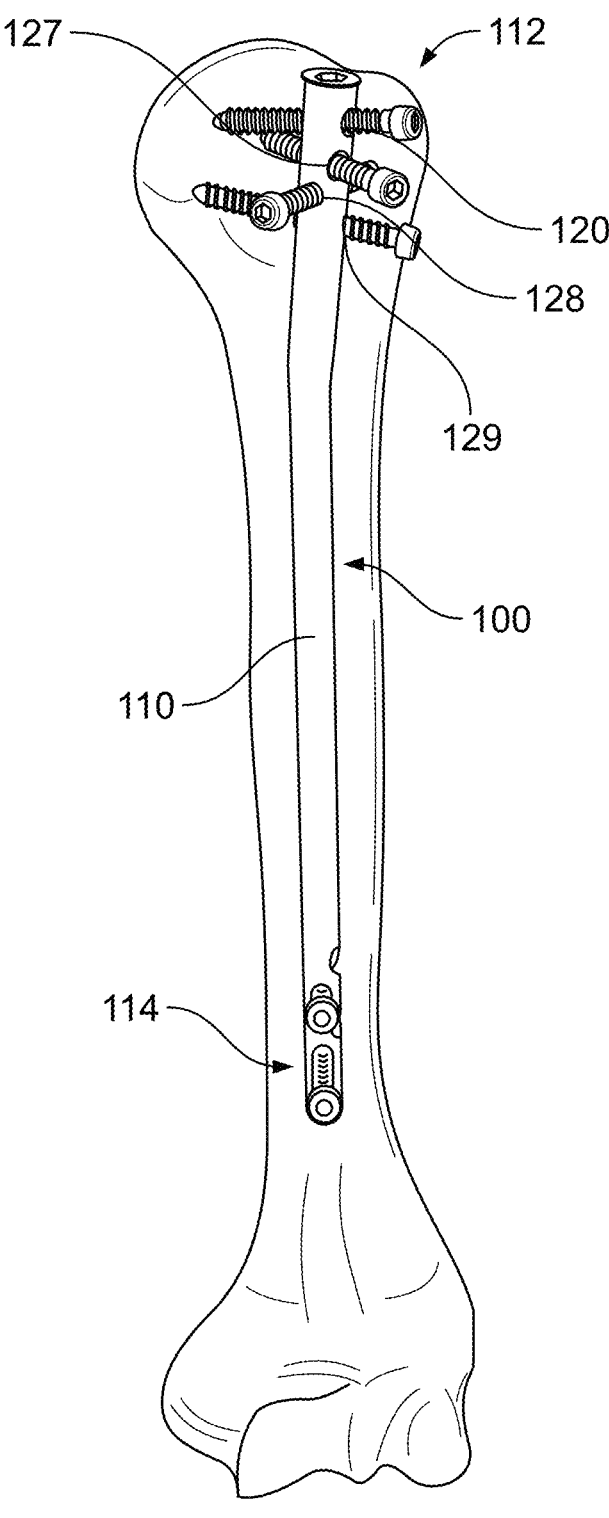
FIG. 1 is a perspective view of an embodiment of a surgical assembly.
Figure 2:
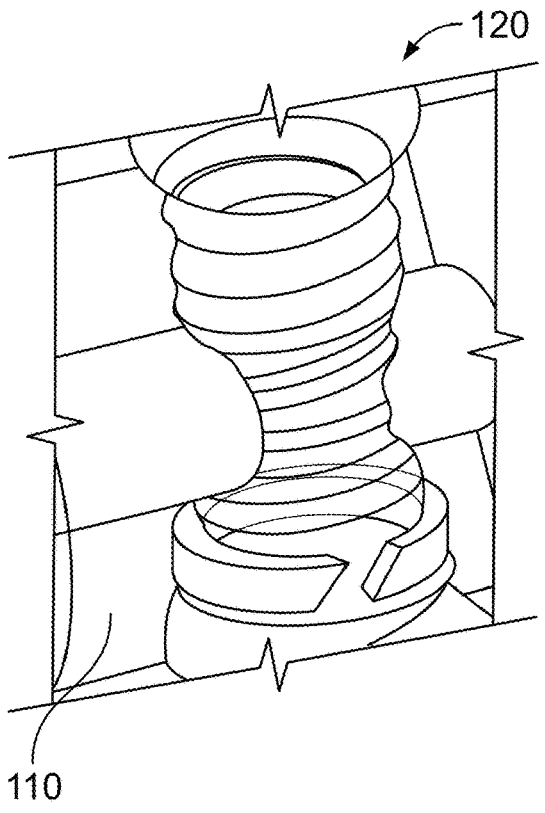
FIG. 2 is a perspective view of a portion of an intramedullary nail and a locking ring of the surgical assembly shown in FIG. 1.
Figure 3:
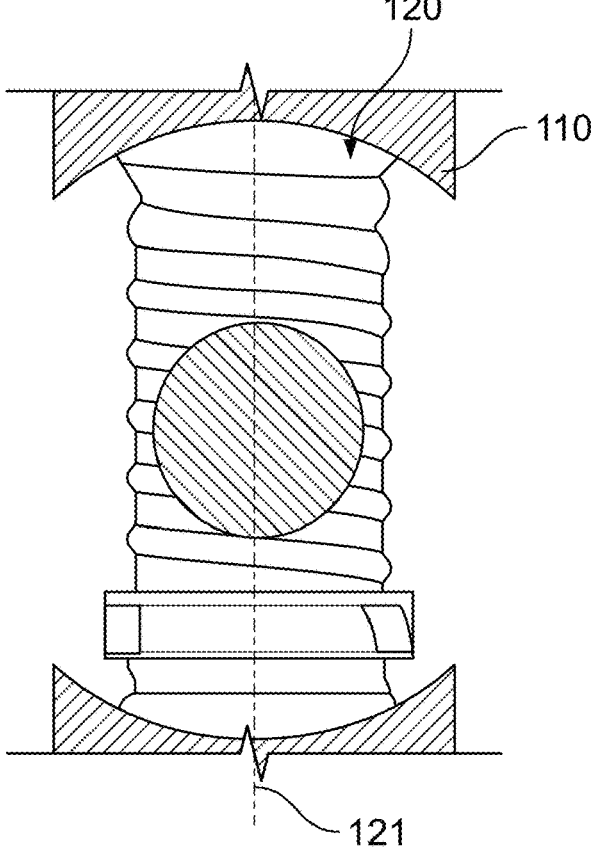
FIG. 3 is a sectional view of a portion of the intramedullary nail and the locking ring of the surgical assembly shown in FIG. 1.

As shown in FIGS. 1-3, a first embodiment of the present invention is an intramedullary nail 100 for use in the proximal humerus. Nail 100 may also be used or adapted for use in other long bones, such as the femur, tibia, etc., and may be used as shown or configured as optimal for the particular bone. Nail 100 includes a body 110 extending from a proximal end 112 to a distal end 114, as shown in FIG. 1. Body 110 defines several transverse bores, including a transverse bore 120 extending along a transverse bore axis 121 through body 110 and generally perpendicular to the axis along which body 110 extends.

Figures 10, 11, 12, 13, 14:
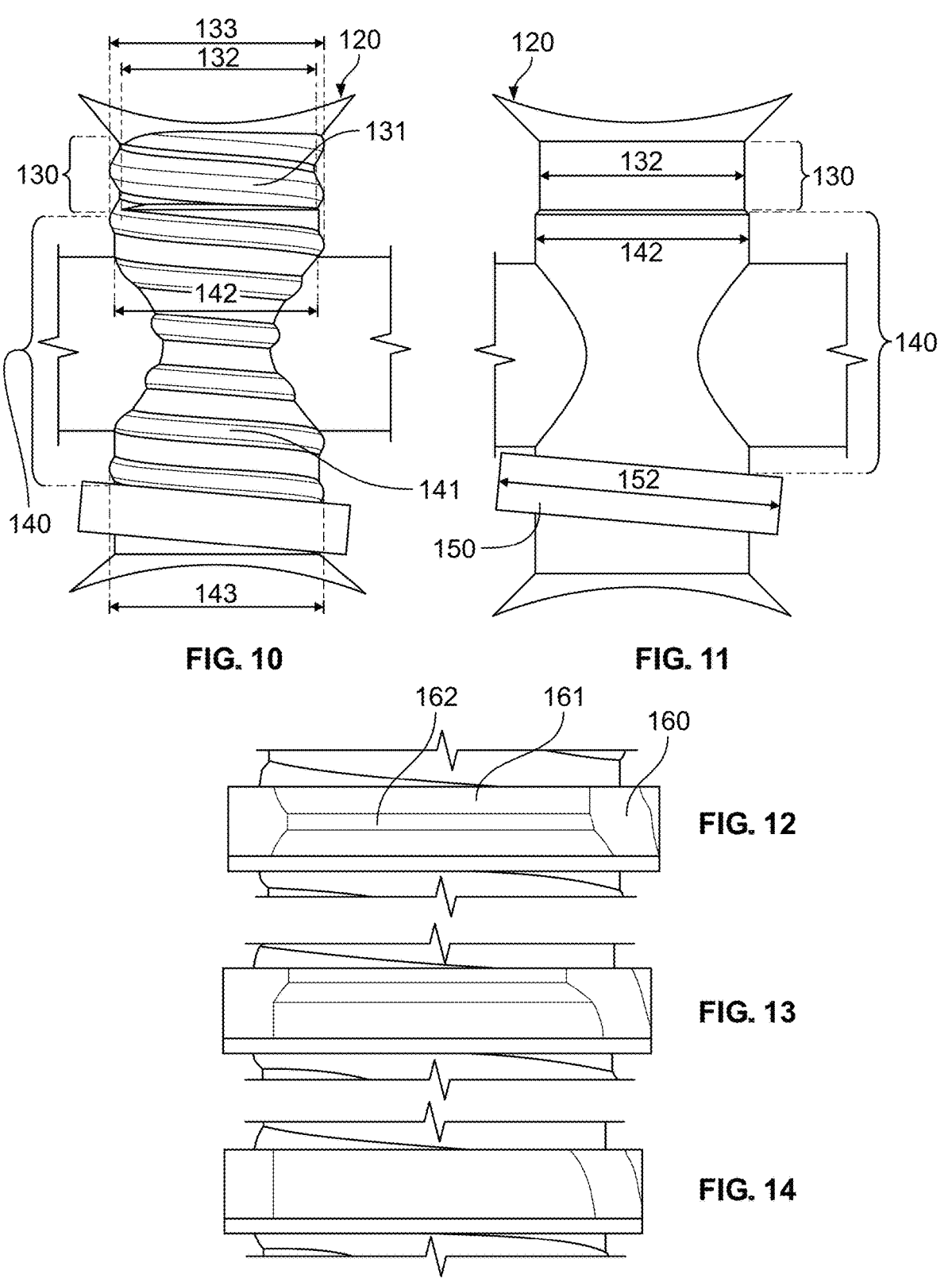
FIGS. 10 and 11 are sectional views of a portion of the intramedullary nail shown in FIG. 1, with and without a depiction of the threads, respectively.
FIGS. 12-14 are sectional views of different embodiments of a locking ring.

Bore 120 is comprised mainly of two segments situated along transverse bore axis 121, as shown in FIGS. 10 and 11. A first segment 130 shown at the top of the figures has a negative thread 131 defined by a first segment root diameter 132 and a first segment outer thread diameter 133. First segment outer thread diameter 133 is larger than first segment root diameter 132, as first segment outer thread diameter 133 represents the distance from the central axis of the bore, past first segment root diameter 132, to the greatest depth of negative thread 131 extending into the material of nail 100. First segment root diameter 132, which is also shown in a schematic of FIG. 11 where bore 120 is depicted without threads, is the largest diameter of an unthreaded cylinder that would fit within first segment 130. First segment outer thread diameter 133 is the outer diameter of negative thread 131 extending outward from such a cylinder. In one embodiment, first segment root diameter 132 is 3.9 mm and first segment outer thread diameter 133 is 4.25 mm. A length of first segment 130 along transverse bore axis 121 is 1.3 mm in one embodiment, and can be in a range of 1.0-1.5 mm, or in a range of 0.5-2.5 mm.

Bore 120 transitions from first segment 130 to a second segment 140 that is also threaded with a negative thread 141 defined by a second segment root diameter 142 and a second segment outer thread diameter 143. Second segment outer thread diameter 143 is larger than second segment root diameter 142 and similarly represents the distance from the central axis of the bore, past second segment root diameter 142, to the greatest depth of negative thread 141 extending into the material of nail 100. Second segment root diameter 142 is the largest diameter of an unthreaded cylinder that would fit within second segment 140. Second segment outer thread diameter 143 is the outer diameter of negative thread 141 extending outward from such a cylinder. In one embodiment, second segment root diameter 142 is 4.1 mm and first segment outer thread diameter 133 is 4.25 mm, which in this case is equal to first segment outer thread diameter 133. As these particular dimensions show, second segment root diameter 142 is larger than first segment root diameter 132. This creates an additional annular space between the transverse bore axis 121 and negative thread 141 in second segment 140 as compared to first segment 130. In other words, the unthreaded cylinder defined by second segment root diameter 142 is larger than the unthreaded cylinder defined by first segment root diameter 132. A length of second segment 140 along transverse bore axis 121 is 6.0 mm in one embodiment, and can be in a range of 5.5-6.5 mm, or in a range of 4.25 mm-7.75 mm. In one embodiment, the length of second segment 140 is larger than first segment outer thread diameter 133 and shorter than the outer diameter of nail 100 at the bore 120.

Negative threads 131 and 141 together form a single continuous negative or virtual thread along bore 120. In this way, first segment 130 and second segment 140 are abutted as shown in FIG. 11 such that the single virtual thread crosses the transition between the segments 130, 140. Negative threads 131 and 141 of first and second segments 130, 140 have identical thread pitches, though the pitches can also be different in other embodiments.

An annular recess 150 is also provided within bore 120. Annular recess 150 has a recess diameter 152 larger than both second segment root diameter 142 and first segment root diameter 132, and also larger than second segment outer thread diameter 143 and first segment outer thread diameter 133. Annular recess 150 may be disposed within second segment 140 so that recess 150 is between the ends of second segment 140 and therefore interrupts negative thread 141. In other embodiments, annular recess 150 may be disposed outside of second segment 140 at an end of second segment 140 opposite of first segment 130. Annular recess 150 itself is not threaded, but provides an annular space in which to hold a locking ring, discussed below. Annular recess 150 may be angled with respect to transverse bore axis 121 or may be perpendicular thereto. In the embodiments of nail 100, first segment 130, second segment 140, and annular recess 150 (which may be within second segment 140 or separate from and adjacent to second segment 140) make up an entirety (i.e. spans the entire length) of bore 120, not accounting for any chamfers or leading ends at either opening of bore 120.

As shown in FIG. 1, additional bores 127, 128, and 129 are provided at proximal end 112 of nail 100, and each can be dimensioned identically to bore 120. In other embodiments, the principal constructions and configurations of bores 120, 127, 128, and 129 are the same though the dimensions and ratios may be different. In other embodiments, any or all of bores 127, 128, and 129 can be conventionally threaded bores.

Figure 5:
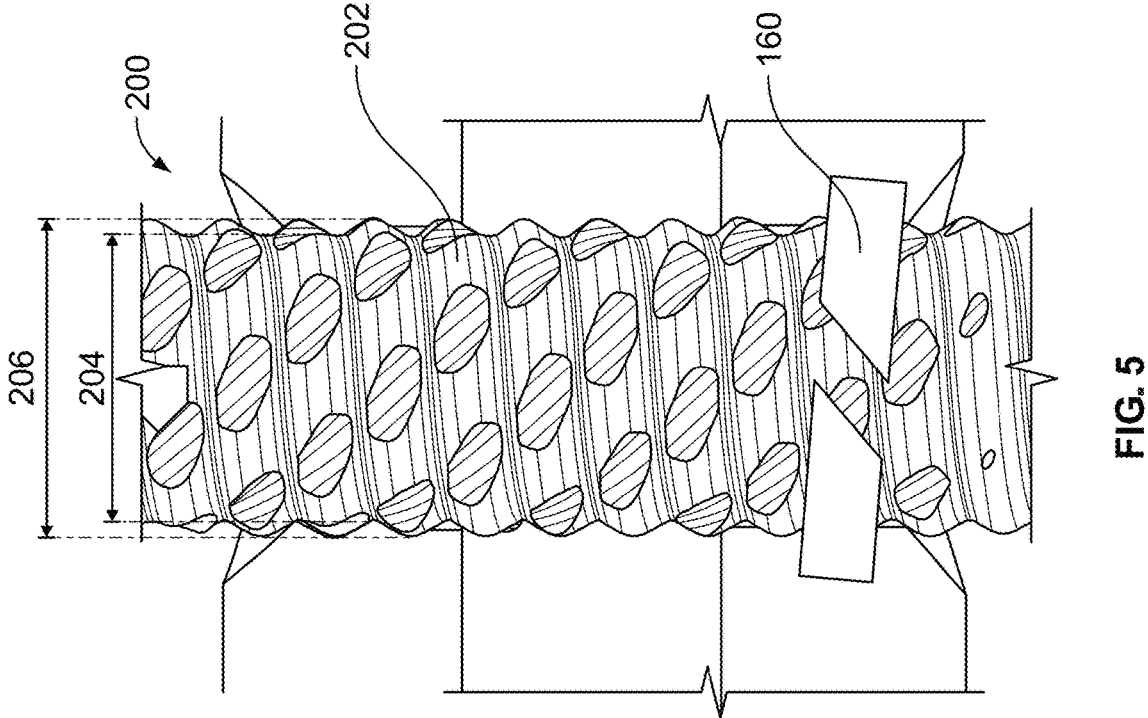
FIG. 5 is a sectional view of a portion of the intramedullary nail and the locking ring of the surgical assembly shown in FIG. 1 together with another screw.
Figure 4:
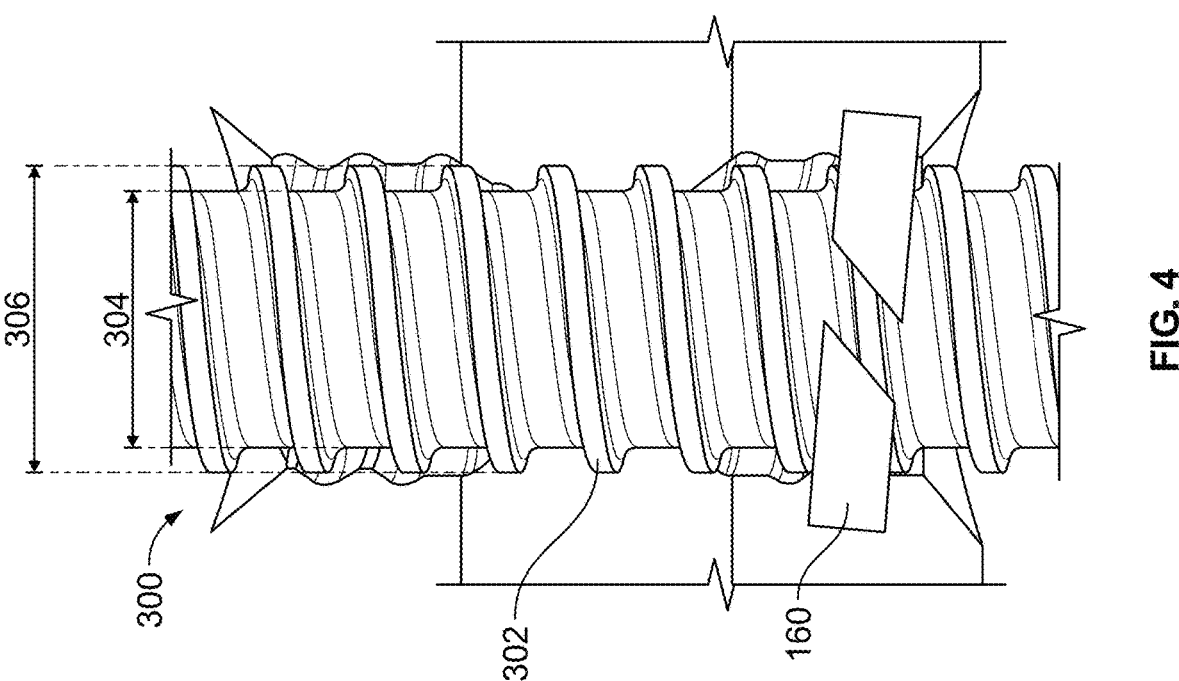
FIG. 4 is a sectional view of a portion of the intramedullary nail and the locking ring of the surgical assembly shown in FIG. 1 together with a screw.

Nail 100 can be part of a surgical assembly as shown in FIGS. 4 and 5 that also includes a locking ring 160 configured to be disposed within annular recess 150. Locking ring 160 is comprised of an elastic material such as a polymer or other surgical grade flexible material. Locking ring 160 is a split ring such that it is slotted to form an incomplete annulus. In this way, locking ring 160 can be flexed and compressed to relatively smaller and larger diameters to facilitate insertion into annular recess 150 during assembly with nail 100. As shown in FIGS. 12-14, different versions of a locking ring 160 each have an inner surface 161 on which a thread or ridge 162 is disposed for contacting a screw. In FIG. 12, the thread/ridge 162 is disposed in a middle of the ring 160. In FIG. 13, the thread/ridge 162 is disposed at a top of the ring 160. In FIG. 14, the thread/ridge is disposed at one lateral side or edge of ring 160 so that the top portion of the passage through ring 160 is smaller in size than any lower portion of the passage through ring 160. Other variations of the size and location of thread/ridge 162 are possible in different embodiments of ring 160. Ultimately, ring 160 permits two different screws with different outer diameters, inner diameters, and/or pitches to interact with ring 160 to create rotational friction to prevent the screw or fastener from unintended rotation, despite the different configurations of the fasteners.

Figure 7:
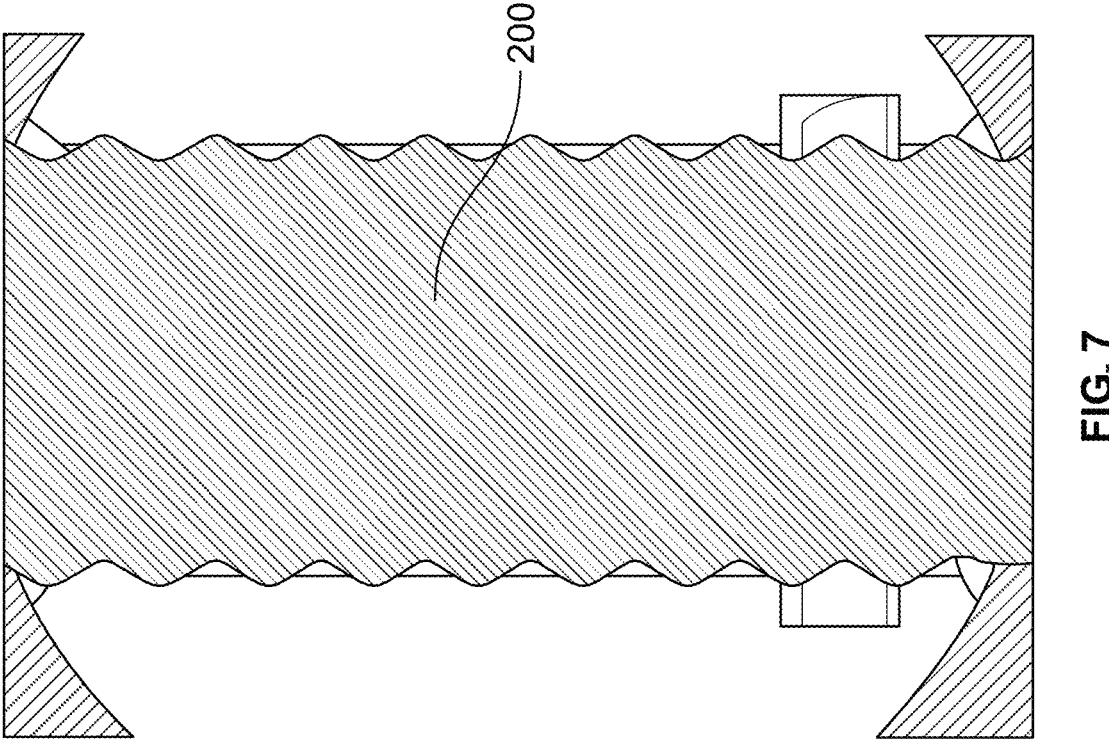
FIG. 7 is a sectional view of the assembly and the screw shown in FIG. 5.
Figure 8:
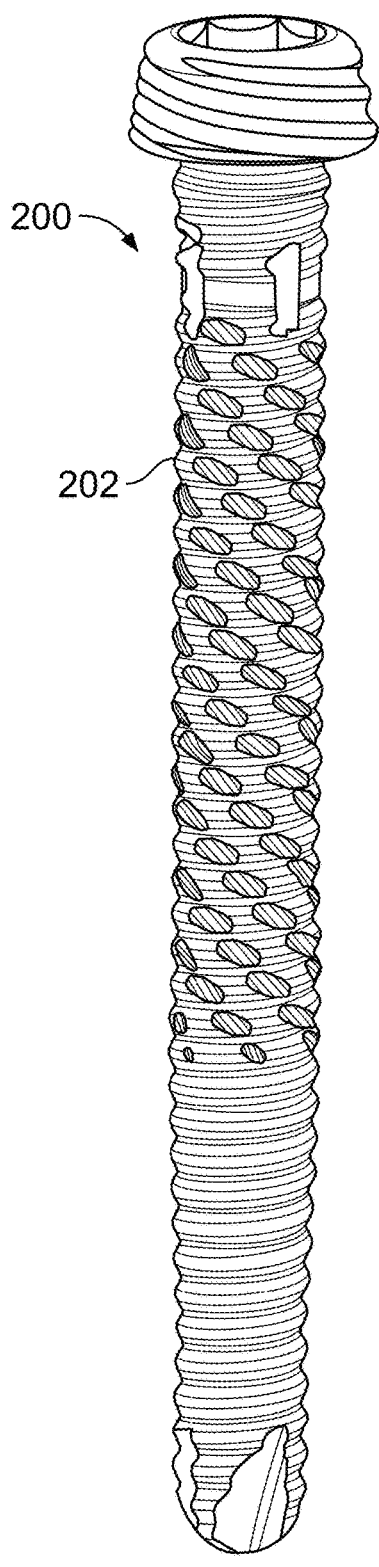
FIG. 8 is a perspective view of the screw shown in FIG. 5.

In another surgical assembly, nail 100 is provided in connection with a first screw 200, as shown in FIGS. 5, 7, and 8. First screw 200 has a threaded portion or shaft 202 defining a root diameter 204, an outer thread diameter 206, and a pitch. In one embodiment, root diameter 204 is 3.8 mm, outer thread diameter 206 is 4.25 mm, and the pitch of first screw 200 is 1.0 mm. First screw 200 can be of the type disclosed in U.S. Pat. No. 11,116,557, the entire disclosure of which is hereby incorporated herein by reference. Bore 120 of nail 100 is designed in conjunction with first screw 200, such that outer thread diameter 206 of threaded portion 202 of first screw 200 is greater than second segment root diameter 142. In that way, threaded portion 202 can be disposed within negative threads 131, 141 of both first segment 130 and second segment 140 of bore 120. In other words, the entire length of the virtual thread including negative threads 131, 141 is an interaction zone for threaded portion 202 of first screw 200. The pitch of threaded portion 202 is substantially the same as and may be equal to the pitch of the virtual thread within bore 120.

Figure 6:
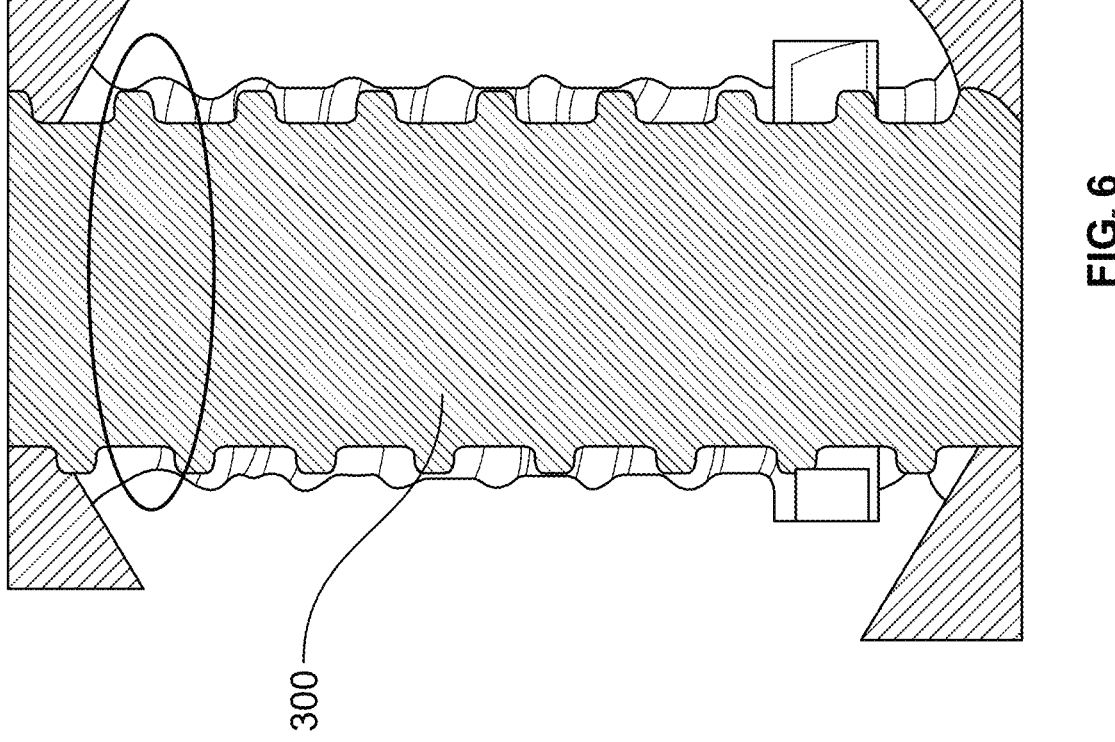
FIG. 6 is a sectional view of the assembly and the screw shown in FIG. 4.
Figure 9:
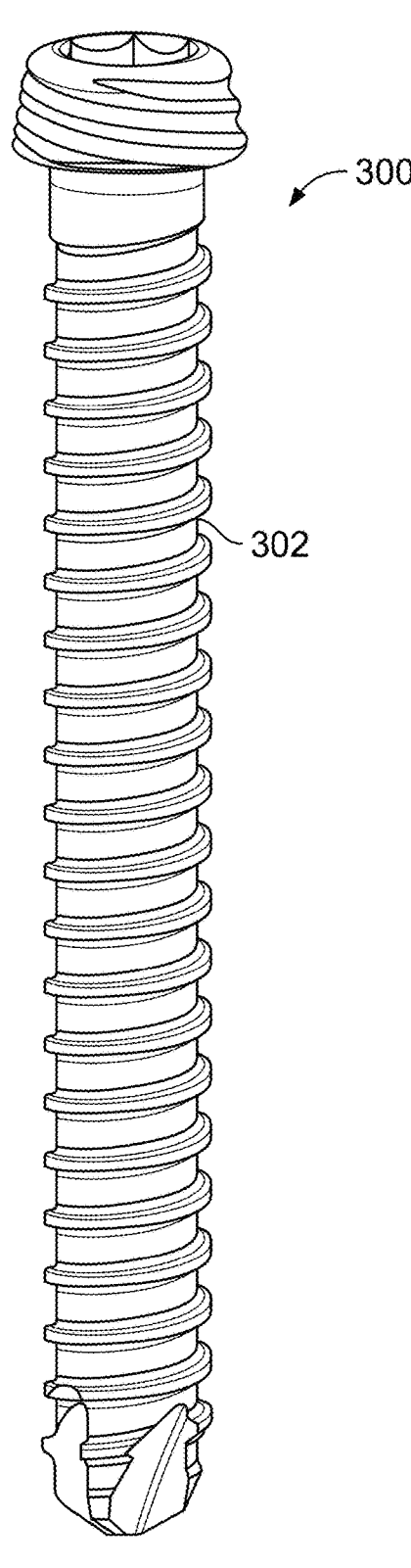
FIG. 9 is a perspective view of the screw shown in FIG. 4.

The surgical assembly can further include a second screw 300, as shown in FIGS. 4, 6, and 9. Like first screw 200, second screw 300 has a threaded portion or shaft 302 defining a root diameter 304, an outer thread diameter 306, and a pitch. In one embodiment, root diameter 304 is 3.8 mm, outer thread diameter 306 is 4.0 mm, and the pitch of second screw 300 is 1.25 mm. Outer thread diameter 306 is different, i.e. less than, outer thread diameter 206 of first screw 200 for reasons explained below. Overall, the profile of second screw 300 is different than the profile of first screw 200.

The same bore 120 of nail 100 is also designed in conjunction with second screw 300 but to interact differently than it does with first screw 200 so that both screws 200 and 300 may be accommodated and fixed appropriately within bore 120 during a surgical procedure. That is, bore 120 is designed to interact with both first screw 200 and second screw 300, yet in different ways, to provide more options for the surgeon to utilize the proper screw in the proper location of nail 100 based on the surrounding bone size, density, and quality. Outer thread diameter 306 of threaded portion 302 of second screw 300 is greater than first segment root diameter 132 and smaller than second segment root diameter 142. In this way, threaded portion 302 of second screw 300 can be disposed within negative thread 131 of the first segment 130 of bore 120 to positively interact with first segment 130. Yet threaded portion 302 of second screw 300 is dimensioned so that it cannot be disposed within negative thread 141 of second segment 140 of bore 120, as shown in FIG. 4. In other words, second screw 300 only interacts with a part of the length of the virtual thread, i.e. negative thread 131.

The pitch of second screw 300 is different than the pitch of first screw 200. While the pitch of threaded portion 202 of first screw 200 is substantially the same as and may be equal to the pitch of the virtual thread within bore 120, including negative thread 131, bore 200 is also designed to accommodate threaded portion 302 of second screw 300 for a secure connection. That is, first portion 130 provides an interaction zone for second screw 300, as shown in FIG. 4. The length of first portion 130 is short enough so that the difference between the pitch of negative thread 131 and the pitch of threaded portion 302 of second screw 300 is negligible. In one embodiment, the length of first portion 130 of bore 120 is not shorter than the distance from crest to crest of threaded portion 302 of second screw 300, i.e. the pitch of threaded portion 302. The smaller diameter in the opposing wall of nail 100 at first portion 130 is intended to provide grip and movement for second screw 300 while also allowing the thicker first screw 200 to pass. In this way, second portion 140 interacts with first screw 200 while providing a free space and no interaction with second screw 300.

In one particular configuration of the surgical system, two identical or substantially similar bores 120 can be provided in nail 100, and first and second screws 200, 300 are respectively disposed within the separate bores 120. Each bore 120 can further include a locking ring 160 as described above and disposed within the respective annular recess 150, as shown in FIGS. 4 and 5. In such a configuration, first screw 200 interacts with the entire virtual thread throughout bore 120 as well as with inner surface 161 of locking ring 160. Second screw 300 interacts with only first portion 130 of bore 120 and the inner surface 161 of locking ring 160. Annular recess 150 provides space for the elastic material of locking ring 160 to create friction against both screws 200 and 300, but particularly second screw 300 which is otherwise not secured to the material of nail 100 at the distal end of bore 120. Thus, locking ring 160 accommodates both screws 200 and 300 while compensating for their different pitches and diameters. Locking ring 160 creates friction between the respective screw and nail 100 to prevent rotation and backout.

A method of using a system including nail 100, locking ring 160, and first screw 200 and/or second screw 300 includes first preparing the bone for accepting nail 100 and inserting nail 100 within the intramedullary canal using known procedures. Prior to insertion of nail 100, locking ring is placed within annular recess 150 by compressing ring 160 and guiding it into recess 150, at which time the elastic material of ring 160 expands outward to a resting state or to be in contact with an outer perimeter of recess 150. In this way, ring 160 is fully seated within recess 150 of nail 100.

Preparations are made to insert a fastener into bore 120 by conventional methods, including use of an alignment arm and a targeting device, insertion of a k-wire, and drilling a hole in the bone to align with bore 120. If first screw 200 is chosen for use with nail 100, shaft 202 is inserted through bone and into bore 120. As it is inserted, threaded portion 202 of first screw 200 interacts with the entire length of the virtual thread including negative threads 131, 141. The pitch of threaded portion 202 is substantially the same as the pitch of negative thread 131, and outer thread diameter 206 of threaded portion is also substantially the same as first segment outer thread diameter 133, thus ensuring a tight and secure fit of first screw 200 within first segment 130 of bore 120. Outer thread diameter 206 of threaded portion 202 is also greater than second segment root diameter 142, and indeed substantially the same as second segment outer thread diameter 143, thus securing a further tight and secure fit of first screw within second segment 140 of bore 120 as well. Threaded portion 202 also contacts locking ring 160 and engages thread or ridge 162, which may compress ring 160 into annular recess 150 based on the dimensional tolerances. This provides additional friction to lock first screw 200 in its inserted position. In addition, threaded portion 202 may cut through thread or ridge 162 to further enhance fixation.

If second screw 300 is chosen, threaded shaft 302 is inserted through bone and into bore 120. During this insertion, threaded shaft 302 positively interacts with first segment 130 since outer thread diameter 306 of threaded portion 302 is greater than first segment root diameter 132. Despite the difference in pitch between threaded shaft 302 and negative thread 131, the relatively short length of first portion 130 permits a connection therebetween to provide fixation of second screw 300 within first portion 130. As second screw 300 is inserted further, since outer thread diameter 306 of threaded portion 302 is smaller than second segment root diameter 142, there is no interaction of threaded portion 302 with second segment 140 of bore. However, ring 160 is dimensioned such that its thread or ridge 162 is of a smaller diameter than outer thread diameter 306. Accordingly, threaded portion 302 contacts locking ring 160 and engages thread or ridge 162, which may compress ring 160 into annular recess 150 to provide friction to lock second screw 300 in its inserted position. Threaded portion 302 may also cut through thread or ridge 162 to provided additional fixation.

Accordingly, bore 120 is dimensioned and configured to accept either first screw 200 or second screw 300 and to provide fixation for either of these differently dimensioned screws. When locking ring 160 is utilized within annular recess 150, additional fixation at the distal end of bore 120 is provided for both screws 200, 300. This permits a surgeon to utilized one of a different selection of screws or fixation devices within a single bore. Of course, assuming more than one bore 120 is provided in nail 100, each with or without a locking ring 160, the surgeon can choose to place similar or different screws within the various bores 120.

The nails and screws disclosed herein can each be made of any surgical grade rigid material such as plastic, ceramic, or metal, and particularly various metals such as titanium, titanium alloys, stainless steel, cobalt chrome alloys, tantalum and niobium, or any combination thereof. Gold and/or silver can be provided in the material composition or as a coating of a component. Each component of the present invention may be formed by an additive manufacturing process, including but not limited to electron beam melting (EBM), selective laser sintering (SLS), selective laser melting (SLM), binder jet printing, and blown powder fusion for use with metal powders.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intramedullary nail comprising:
a body extending from a proximal end to a distal end, the body defining a transverse bore extending through the body along a transverse bore axis,
the transverse bore having a threaded first segment with a negative thread defined by a first segment root diameter and a first segment outer thread diameter,
the transverse bore having a threaded second segment with a negative thread defined by a second segment root diameter and a second segment outer thread diameter,
wherein the second segment root diameter is larger than the first segment root diameter, and
wherein the transverse bore further includes an annular recess having a recess diameter larger than the second segment root diameter.

2. The intramedullary nail of claim 1, wherein the threaded first and second segments are abutted such that the negative threads of the threaded first and second segments form a continuous negative thread.

3. The intramedullary nail of claim 1, wherein the threaded first segment and the threaded second segment have identical thread pitches.

4. The intramedullary nail of claim 1, wherein the first segment outer thread diameter is equal to the second segment outer thread diameter.

5. The intramedullary nail of claim 1, wherein the recess diameter is larger than the second segment outer thread diameter.

6. The intramedullary nail of claim 1, wherein the annular recess is disposed between ends of the threaded second segment.

7. The intramedullary nail of claim 1, wherein the threaded first and second segments and the annular recess make up an entirety of the transverse bore.

8. A surgical assembly comprising:
the intramedullary nail of claim 1; and
a locking ring configured to be disposed within the annular recess.

9. The surgical assembly of claim 8, wherein the locking ring is comprised of an elastic material.

10. The surgical assembly of claim 9, wherein the elastic material is a polymer.

11. The surgical assembly of claim 8, wherein the locking ring is slotted such that the locking ring forms an incomplete annulus.

12. The surgical assembly of claim 8, wherein the locking ring has an inner surface on which a thread is disposed.

13. A surgical assembly comprising:
an intramedullary nail comprising:
a body extending from a proximal end to a distal end, the body defining a transverse bore extending through the body along a transverse bore axis,
the transverse bore having a threaded first segment with a negative thread defined by a first segment root diameter and a first segment outer thread diameter, the transverse bore having a threaded second segment with a negative thread defined by a second segment root diameter and a second segment outer thread diameter, wherein the second segment root diameter is larger than the first segment root diameter; and a first screw having a threaded portion defining a root diameter, an outer thread diameter, and a pitch, wherein the outer thread diameter of the threaded portion of the first screw is greater than the second segment root diameter, such that the threaded portion of the first screw is disposed within the negative threads of both the threaded first and second segments of the transverse bore when the first screw is disposed within the transverse bore.

14. The surgical assembly of claim 13, further comprising:

a second screw having a threaded portion defining a root diameter, an outer thread diameter, and a pitch, wherein the outer thread diameter of the threaded portion of the second screw is greater than the first segment root diameter and smaller than the second segment root diameter, such that the threaded portion of the second screw is disposed within the negative thread of the threaded first segment of the transverse bore and is not disposed within the negative thread of the threaded second segment of the transverse bore when the first screw is disposed within the transverse bore.

15. The surgical assembly of claim 14, wherein the transverse bore further includes an annular recess having a recess diameter larger than the second segment root diameter, and further comprising a locking ring configured to be disposed within the annular recess.

16. The surgical assembly of claim 14, wherein:

the pitch of the second screw is different than the pitch of the first screw, the outer thread diameter of the second screw is different than the outer thread diameter of the first screw, and/or the root diameter of the second screw is different than the root diameter of the first screw.

17. The surgical assembly of claim 14, wherein the transverse bore includes first and second identically configured transverse bores.

18. The surgical assembly of claim 17, wherein the first screw is disposed within the first transverse bore and the second screw is disposed within the second transverse bore.

19. The surgical assembly of claim 18, wherein each of the first and second transverse bores further includes an annular recess having a recess diameter larger than the respective second segment root diameter, wherein the surgical assembly further comprises first and second locking rings disposed within the annular recesses of the first and second transverse bores, respectively.

\*    \*    \*    \*    \*